United States Patent [19]

Macy et al.

[11] Patent Number: 5,723,447
[45] Date of Patent: Mar. 3, 1998

[54] WATER MISCIBLE ERYTHROMYCIN SOLUTIONS

[75] Inventors: Lowell R. Macy, Vermillion, S. Dak.; Raymond E. Hopponen, Fort Dodge, Iowa

[73] Assignee: Rhone Merieux, Inc., Athens, Ga.

[21] Appl. No.: 675,380

[22] Filed: Jul. 2, 1996

[51] Int. Cl.⁶ .................................................. A61K 31/70
[52] U.S. Cl. .................................. 514/29; 536/7.2
[58] Field of Search .................. 514/29; 536/7.2

[56] References Cited

U.S. PATENT DOCUMENTS 5,175,150  12/1992  Omera et al. ............................. 514/29

*Primary Examiner*—Elli Peselev
*Attorney, Agent, or Firm*—Frommer Lawrence & Haug LLP; William S. Frommer

[57] ABSTRACT

Water miscible pharmaceutical compositions containing up to about 40% of erythromycin prepared by reaction with acetic acid in a non-aqueous water miscible organic solvent system.

14 Claims, No Drawings

WATER MISCIBLE ERYTHROMYCIN SOLUTIONS

FIELD OF THE INVENTION

This invention relates to antibiotic compositions suitable for pharmaceutical use and in particular to water miscible solutions of the antibiotic erythromycin.

BACKGROUND OF THE INVENTION

Erythromycin (MW 733.94 daltons) is the common name for a macrolide antibiotic produced by the growth of a strain of Streptomyces erythreous. It is a mixture of three erythromycins, A, B and C consisting largely of erythromycin A which is represented by the formula, $(3R^*,4S^*,5S^*,6R^*,7R^*,9R^*,11R^*,12R^*,13S^*,14R^*)$-4-[(2,6-dideoxy-3-C-methyl-3-O-methyl-$\alpha$-L-ribo-hexopyranosyl)-oxy]-14-ethyl-7,12,13-trihydroxy-3,5,7,9,11,13-hexamethyl-6[[3,4,6-trideoxy-3-(dimethylamino)-$\beta$-D-xylo-hexapyranosyl]oxy]oxacyclotetradecane-2,10-dione, $(C_{37}H_{67}NO_{13})$.

Erythromycin has a broad and essentially bacteriostatic action against many Gram-positive and some Gram-negative bacteria as well as other organisms including mycoplasmas, spirochetes, chlamydiae and rickettsiae. In humans, it finds usefulness in the treatment of a wide variety of infections. It finds wide application in veterinary practice in the treatment of infectious diseases such as pneumonias, mastitis, metritis, rhinitis, and bronchitis in cattle, swine and sheep.

Erythromycin is soluble in many organic solvents but is only slightly water soluble. Solutions of erythromycin in organic solvent systems are used in veterinary practice for administration by the intramuscular and subcutaneous routes. They cannot be used for intravenous administration because the erythromycin precipitates when the solution is introduced into an aqueous medium as into body fluids. Aqueous solutions of erythromycin salts can be prepared but have such limited stability as to be limited to use for only a short time period after preparation.

A water miscible solution of erythromycin which would be stable for an extended period of time would be of great value to the veterinary profession. It could be used for intravenous administration to rapidly provide therapeutic blood levels for more effective treatment of infectious diseases. A water miscible solution would also allow for more rapid absorption from intramuscular and subcutaneous injection sites leading to higher concentrations in body fluids and more effective control of infectious diseases. Such a solution would also be useful for oral administration to poultry and swine in their drinking water.

DESCRIPTION OF THE PREFERRED EMBODIMENTS

The present invention provides a stable, high potency water miscible formulation of erythromycin. Erythromycin contains a basic nitrogen grouping which can be converted in non aqueous solutions into stable water miscible compositions by the addition of acetic acid. The resulting compositions are stable for extended periods of time and do not lead to precipitation of the erythromycin when introduced into an aqueous environment. The acetic acid is added in an amount about equimolar to the erythromycin. The acetic acid advantageously is added in an amount at least equimolar to the erythromycin. Solutions containing as much as 40% of erythromycin can be prepared in this manner.

A variety of organic solvents or mixtures of solvents can be used as the vehicles for the compositions. Examples of suitable solvents that can be used include: propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether.

Compositions of the present invention can be readily prepared by adding an amount of acetic acid about equimolar to the desired concentration of erythromycin to the selected organic solvent or solvents. The erythromycin is then added and the mixture stirred until complete solution results.

Thus, the invention relates to a stable water miscible erythromycin composition comprising: a) erythromycin at a concentration of between about 10% and about 40% by weight, based on the volume of the composition; b) acetic acid present in an amount about equimolar to that of the erythromycin and forming a water soluble acetate compound of erythromycin; and c) a water miscible non-aqueous vehicle composed of a suitable organic solvent or mixture of solvents.

Advantageously, the erythromycin is in the form of an erythromycin base.

The composition is advantageously provided in the form of a sterile injectable composition.

The erythromycin preferably is present in a concentration of between about 20% and about 30% by weight based on the volume of the composition.

The vehicle advantageously is composed of propylene glycol monomethyl ether, or dipropylene glycol monomethyl ether, or diethylene glycol ethyl ether, or mixtures thereof. Advantageously, the vehicle is composed of N-methyl pyrrolidone in a concentration of between about 30% and about 50% by volume and the balance is propylene glycol. Preferably, the vehicle is composed of N-methyl pyrrolidone in a concentration of between about 30% and about 50% by volume and the balance is polyethylene glycol 200, or polyethylene glycol 300 or polyethylene glycol 400.

The invention also relates to a stable water miscible erythromycin composition comprising: a) erythromycin at a concentration of between about 10% and about 40% by weight, based on the volume of the composition; b) acetic acid present in an amount at least equimolar to that of the erythromycin and forming a water soluble acetate compound of erythromycin; and c) a water miscible non-aqueous vehicle composed of a suitable organic solvent or mixture of solvents.

The invention further relates to a method of preparing a stable, high potency water miscible erythromycin composition comprising the steps of: a) preparing a non-aqueous vehicle of a water miscible organic solvent or solvents; b) adding acetic acid in a concentration of between 0.9 and 1.1 molar with respect to the desired concentration of erythromycin; and c) combining the acetic acid solution with erythromycin in order to achieve a final concentration of between about 10% and about 40% by weight of erythromycin.

EXAMPLE

One liter of a 20% solution of erythromycin was prepared according to the following procedure:

| Erythromycin (based on a potency of 910 micrograms per milligram) | |
|---|---|
| $\frac{200 \text{ g}}{0.910} =$ | 219.8 g |
| Glacial acetic acid | 16.4 g |
| N-methyl pyrrolidone | 400.0 mL |
| Propylene glycol | qs 1000.0 mL |

The glacial acetic acid was added to a mixture of the N-methyl pyrrolidone and 300 mL of propylene glycol and mixed. The erythromycin was added slowly with stirring. When the erythromycin was completely dissolved, the solution was brought to volume with propylene glycol.

What is claimed is:

1. A stable water miscible erythromycin composition comprising:
   a) erythromycin at a concentration of between about 10% and about 40% by weight, based on the volume of the composition;
   b) acetic acid present in an amount about equimolar to that of the erythromycin and forming a water soluble acetate compound of erythromycin; and
   c) a water miscible non-aqueous vehicle composed of a organic solvent or mixture of solvents.

2. A composition according to claim 1 wherein the erythromycin is in the form of an erythromycin base.

3. A composition according to claim 1 wherein the composition is provided in the form of a sterile injectable composition.

4. A composition according to claim 1 wherein the erythromycin is present in a concentration of between about 20% and about 30% by weight based on the volume of the composition.

5. A composition according to claim 1 wherein the vehicle is composed of propylene glycol monomethyl ether, or dipropylene glycol monomethyl ether, or diethylene glycol ethyl ether, or mixtures thereof.

6. A composition according to claim 1 wherein the vehicle is composed of N-methyl pyrrolidone in a concentration of between about 30% and about 50% by volume and the balance is propylene glycol.

7. A composition according to claim 1 wherein the vehicle is composed of N-methyl pyrrolidone in a concentration of between about 30% and about 50% by volume and the balance is polyethylene glycol 200, or polyethylene glycol 300 or polyethylene glycol 400.

8. A stable water miscible erythromycin composition comprising:
   a) erythromycin at a concentration of between about 10% and about 40% by weight, based on the volume of the composition;
   b) acetic acid present in an amount at least equimolar to that of the erythromycin and forming a water soluble acetate compound of erythromycin; and
   c) a water miscible non-aqueous vehicle composed of a organic solvent or mixture of solvents.

9. A method of preparing a stable, high potency water miscible erythromycin composition comprising the steps of:
   a) preparing a non-aqueous vehicle of a water miscible organic solvent or solvents;
   b) adding acetic acid in a concentration of between 0.9 and 1.1 molar with respect to the desired concentration of erythromycin; and
   c) combining the acetic acid solution with erythromycin in order to achieve a final concentration of between about 10% and about 40% by weight of erythromycin.

10. A stable water miscible erythromycin composition comprising:
    a) erythromycin at a concentration of between about 10% and about 40% by weight, based on the volume of the composition;
    b) acetic acid present in an amount about equimolar to that of the erythromycin and forming a water soluble acetate compound of erythromycin; and
    c) a water miscible non-aqueous vehicle composed of an organic solvent or mixture of solvents suitable for administration to an animal or human.

11. A composition according to claim 10 wherein the erythromycin is in the form of an erythromycin base.

12. A composition according to claim 10 wherein the composition is provided in the form of a sterile injectable composition.

13. A composition according to claim 10 wherein the erythromycin is present in a concentration of between about 20% and about 30% by weight based on the volume of the composition.

14. A stable water miscible erythromycin composition comprising:
    a) erythromycin at a concentration of between about 10% and about 40% by weight, based on the volume of the composition;
    b) acetic acid present in an amount at least equimolar to that of the erythromycin and forming a water soluble acetate compound of erythromycin; and
    c) a water miscible non-aqueous vehicle composed of an organic solvent or mixture of solvents suitable for administration to an animal or human.

* * * * *